US012636262B2

(12) United States Patent
Vobalaboina et al.

(10) Patent No.: US 12,636,262 B2
(45) Date of Patent: May 26, 2026

(54) PROCESS FOR THE PREPARATION OF TOPICAL FORMULATION

(71) Applicant: Neuheit Pharma Technologies Pvt. Ltd, Hyderabad (IN)

(72) Inventors: Venkateswarlu Vobalaboina, Hyderabad (IN); Vijaykumar Nagabandi, Hyderabad (IN); Pankaj Chatki, Hyderabad (IN); Niroop Lakkapatri, Hyderabad (IN); Pratibhanusha Chepuru, Hyderabad (IN)

(73) Assignee: Neuheit Pharma Technologies Pvt. Ltd., Hyderabad (IN)

( * ) Notice: Subject to any disclaimer, the term of this patent is extended or adjusted under 35 U.S.C. 154(b) by 1157 days.

(21) Appl. No.: 17/630,775

(22) PCT Filed: Aug. 3, 2020

(86) PCT No.: PCT/IB2020/057309
§ 371 (c)(1),
(2) Date: Jan. 27, 2022

(87) PCT Pub. No.: WO2021/024150
PCT Pub. Date: Feb. 11, 2021

(65) Prior Publication Data

US 2022/0265577 A1 Aug. 25, 2022

(30) Foreign Application Priority Data

Aug. 3, 2019 (IN) ............................. 201941031481

(51) Int. Cl.

| | |
|---|---|
| ***A01N 43/00*** | (2006.01) |
| ***A01N 43/46*** | (2006.01) |
| ***A61K 9/00*** | (2006.01) |
| ***A61K 9/06*** | (2006.01) |
| ***A61K 31/122*** | (2006.01) |
| ***A61K 31/192*** | (2006.01) |
| ***A61K 31/55*** | (2006.01) |
| ***A61K 47/10*** | (2017.01) |
| ***A61K 47/28*** | (2006.01) |

(52) U.S. Cl.
CPC .......... *A61K 31/122* (2013.01); *A61K 9/0014* (2013.01); *A61K 9/06* (2013.01); *A61K 31/192* (2013.01); *A61K 47/10* (2013.01); *A61K 47/28* (2013.01)

(58) Field of Classification Search
None
See application file for complete search history.

(56) References Cited

U.S. PATENT DOCUMENTS 5,952,383 A * 9/1999 Metziger .............. A61K 31/192
514/569

FOREIGN PATENT DOCUMENTS

WO 2009133430 A1 11/2009
WO 2017004319 A1 1/2017

OTHER PUBLICATIONS

Cevc et al (Ultraflexible vesicles, Transfersomes, have an extremely low pore penetration resistance and transport therapeutic amounts of insulin across the intact mammalian skin. Biochimica et Biophysica Acta (BBA)—Biomembranes vol. 1368, Issue 2, Jan. 19, 1998, pp. 201-215) (Year: 1998).*
Malakar et al. (Formulation, optimization and evaluation of transferosomal gel for transdermal insulin delivery. Saudi Pharm J. Oct. 2012;20(4):355-63. doi: 10.1016/j.jsps.2012.02.001. Epub Feb. 21, 2012. PMID: 23960810; PMCID: PMC3744964.) (Year: 2012).*
International Search Report and Written Opinion of International Application No. PCT/IB2020/057309, dated Dec. 4, 2020, 12 pp.

* cited by examiner

*Primary Examiner* — Layla Soroush
(74) *Attorney, Agent, or Firm* — Shumaker & Sieffert, P.A.

(57) ABSTRACT

The present invention relates to the process for the preparation of topical formulations of anthraquinone compound. The present invention specifically relates to the process for the preparation of topical formulations of Rhein or Diacerein in the form of ointment, cream, gel and transferosomal gel. The present invention more specifically relates to the process for the preparation of topical formulations of Rhein or Diacerein in the form of ointment, cream, gel comprising the steps of heating, adding, stirring, dissolving and mixing. The present invention also relates to the process for the preparation of topical formulations of Rhein or Diacerein in the form of transferosomal gel comprising the steps of thin film formation, hydration of thin film and transferosomal gel formation. The present invention also relates to the process for the preparation of topical formulations of Rhein or Diacerein in the form of transferosomal gel comprising the steps of dissolving, adding and mixing.

8 Claims, 5 Drawing Sheets

PROCESS FOR THE PREPARATION OF TOPICAL FORMULATION

This application is a national stage application under 35 U.S.C. § 371 of PCT Application No. PCT/IB2020/057309, filed Aug. 3, 2020, which claims the benefit of IN application No. 201941031481 filed Aug. 3, 2019. The entire contents of each of PCT Application No. PCT/IB2020/057309 and IN application No. 201941031481 are incorporated herein by reference in their entirety.

FIELD OF THE INVENTION

The present invention relates to the process for the preparation of topical formulations of anthraquinone compound.

The present invention also relates to the process for the preparation of topical formulations of Rhein or Diacerein as anthraquinone compound.

The present invention specifically relates to the process for the preparation of topical formulations of Rhein or Diacerein in the form of ointment, cream, gel and transferosomal gel.

The present invention more specifically relates to the process for the preparation of topical formulations of Rhein or Diacerein in the form of ointment, cream, gel comprising the steps of heating, adding, stirring, dissolving and mixing.

The present invention also relates to the process for the preparation of topical formulations of Rhein or Diacerein in the form of transferosomal gel comprising the steps of thin film formation, hydration of thin film and transferosomal gel formation.

The present invention also relates to the process for the preparation of topical formulations of Rhein or Diacerein in the form of transferosomal gel comprising the steps of dissolving, adding and mixing.

BACKGROUND OF THE INVENTION

Osteoarthritis is the most common global chronic joint disease. The disease may affect single or multiple joints and even be generalised. Osteoarthritis is a chronic arthropathy affecting the entire joint, involving the cartilage, joint lining, ligaments, and underlying bone. In osteoarthritis, cartilage loss, osteophyte formation (bone spurs), and subchondral bone sclerosis leads to pain, disability, and a reduction in quality of life. Structural changes, visible by radiography, include narrowing of the joint space, osteophyte formation and bone remodelling around the joints. Osteoarthritis can arise in any synovial joint in the body but is most common in the large joints (knees and hips), hands, and spine.

Inflammation is the body's immediate response to damage to its tissues and cells by pathogens, noxious stimuli such as chemicals or physical injury. Acute inflammation is a short-term response that usually results in healing: leukocytes infiltrate the damaged region, removing the stimulus and repairing the tissue. Chronic inflammation, by contrast, is a prolonged, dysregulated and maladaptive response that involves active inflammation, tissue destruction and attempts at tissue repair.

Rhein is used as hepatoprotective, nephroprotective, anti-inflammatory, antioxidant, anticancer, antimicrobial agent and for treating osteoarthritis.

Rhein is a lipophilic anthraquinone extensively found in medicinal herbs *Rheum palmatum* L., *Cassia tora* L., *Polygonum multiflorum* Thunb and *Aloe barbadensis* Miller. Rhein is commonly found as a glycoside such as rhein-8-glucoside or glucorhein. Rhein was first isolated in 1895. It is found in rhubarb species like *Rheum undulatum* and *Cassia reticulata*. The chemical name of Rhein is 9,10-dihydro-4,5-dihydroxy-9,10-dioxo-2-anthracene carboxylic acid. Rhein has a chemical formula of $C_{15}H_8O_6$ and a molecular mass of 284.22 g/mol. It has a structural formula of:

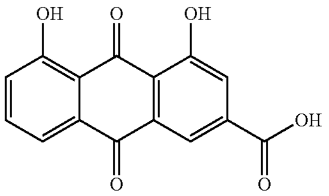 [SMILES: O=C(O)c1cc(O)c2c(c1)C(=O)c1cccc(O)c1C2=O]

Diacerein is also known as diacetyl Rhein, is a slow acting medicine of the class anthraquinone used to treat joint diseases, such as Osteoarthritis. It works by inhibiting interleukin-1 beta. Diacerein works by blocking the actions of interleukin-1 beta a protein involved in the inflammation and destruction of cartilage that play a role in the development of symptoms of degenerative joint diseases. The chemical name of Diacerein is 4,5-diacetyloxy-9,10-dioxo-anthracene-2-carboxylic acid. Diacerein has a chemical formula of $C_{19}H_{12}O_8$ and a molecular mass of 368.29 g/mol. It has a structural formula of:

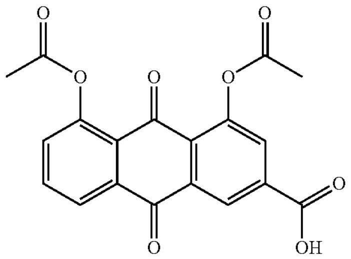 [SMILES: CC(=O)Oc1cccc2c1C(=O)c1c(OC(C)=O)cc(C(=O)O)cc1C2=O]

Diacerein is a pro-drug of rhein widely used as an anti-inflammatory agent in the treatment of osteoarthritis, which acts by inhibiting the interleukin-1 (IL-1) signalling pathway. Diacerein capsules are available in the market as 50 mg strength with different brand names in different countries, including ART 50®, Artrodar® etc.

In the treatment of osteoarthritis, generally rhein is administered orally as its pro-drug Diacerein and where Diacerein is entirely converted into rhein before reaching the systemic circulation. However, the converted rhein is not completely absorbed from the gastro-intestinal tract (GIT) and hence the oral bioavailability Diacerein was reported to be approximately 40-60%. In the lower part of the GIT, the unabsorbed rhein causes undesirable side effects such as diarrhoea or soft stools.

Since the bioavailability of Diacerein through oral route of administration is very less and the unabsorbed rhein is showing laxative effect in the lower part of GIT, these problems can be overcome by applying the formulation containing Diacerein through topical route at the site of osteoarthritis. However, clear reports are not available on conversion of Diacerein to its active form rhein, at the arthritic site or within the blood circulation.

WO2009/133430 discloses topical composition comprising rhein or Diacerein, salts or esters or prodrug thereof and one or more pharmaceutically acceptable excipients selected from emulsifiers, wetting agents or surfactants, chelating agents, solvents, antioxidants, gelling agents, thickening agent or viscosity-enhancing agent waxes, penetration enhancers, solubilizing agents, buffering agents, emollients, bases, coloring agents, flavoring agents and preservatives. It also discloses process for the preparation of a topical composition comprising rhein or Diacerein, salts or esters or prodrug thereof, the process comprising dissolving or suspending rhein or Diacerein, or salts or esters or prodrugs thereof in one or more solvents or bases; and mixing with one or more pharmaceutically acceptable excipients.

WO2017/004319 discloses topical composition comprising a therapeutically effective amount of a compound selected from the group consisting of Diacerein, rhein, monoacetyl rhein, and salts or esters or prodrugs thereof, and one or more pharmaceutically acceptable excipients, wherein the composition is in the form of ointment, cream, or gel, and at least about 90% by volume of the compound has a particle size of about 0.5 to 35 μm.

All the prior art references related to topical composition of Rhein or Diacerein prepared by a process comprising steps of dissolving and mixing. However, the inventors of present invention provide specific process for the preparation of topical formulations of anthraquinone compound. The inventors of present invention also provide specific process for the preparation of topical formulations of Rhein or Diacerein as anthraquinone compounds in the form of ointment, cream, gel comprising the steps of heating, adding, stirring, dissolving and mixing and transferosomal gel comprising the steps of thin film formation, hydration of thin film and transferosomal gel formation. The inventors of present invention also provide specific process for the preparation of Transferosomal gel formation comprises the steps of dissolving, adding and mixing.

OBJECTIVE OF INVENTION

The main objective of the present invention is to provide process for the preparation of topical formulations of anthraquinone compound.

Another objective of the present invention is to provide process for the preparation of topical formulations of Rhein or Diacerein as anthraquinone compounds.

Another objective of the present invention is to provide process for the preparation of topical formulations of Rhein or Diacerein in the form of ointment, cream, gel and transferosomal gel.

Yet another objective of the present invention is to provide specific process for the preparation of topical formulations of Rhein or Diacerein in the form of ointment, cream and gel comprising the steps of heating, adding, stirring, dissolving and mixing.

Still another objective of the present invention is to provide specific process for the preparation of topical formulations of Rhein or Diacerein in the form of transferosomal gel comprising the steps of thin film formation, hydration of thin film and transferosomal gel formation.

Still another objective of the present invention is to provide specific process for the preparation of topical formulations of Rhein or Diacerein in the form of transferosomal gel comprising the steps of dissolving, adding and mixing.

Still another objective of the present invention is to provide process for the preparation of topical formulations of anthraquinone compound in the form of ointment or cream or gel comprising the steps providing a solution of anthraquinone compound, adding other excipients selected from penetration enhancer, humectant, thickening agent, preservatives, ointment base, emulsifying agent, oil phase vehicle adjusting the pH of the medium with pH adjusting agent, and adding water and mixing to form ointment or cream or gel.

Still another objective of the present invention is to provide process for the preparation of topical formulations of anthraquinone compound in the form of transferosomal gel, wherein the process comprising the steps of:

a) thin film formation: dissolving vesicle forming lipid, surfactant in organic solvent, dissolving 60% of anthraquinone compound in obtained organic solvent mixture, evaporating obtained solvent mixture to get thin film,
b) hydration of thin film: dissolving remaining 40% of anthraquinone compound in phosphate buffer (pH 7.4), dissolving preservatives in the obtained anthraquinone compound solution, adding formed aqueous phase to the thin film obtained in step a) to form transferosomes (vesicular systems), evaporating, sonicating to get uniform unilamellar vesicles, and
c) transferosomal gel: adding thickening agent to the obtained vesicles of step b) and adjusting the pH with triethanolamine to 4.0-6.0 to form viscous gel.

Still another objective of the present invention is to provide process for the preparation of topical formulations of anthraquinone compound in the form of transferosomal gel, wherein the process comprising the steps of:

(a) dissolving anthraquinone compound in molten surfactant at 60° C., adding other vesicle forming lipid component and fluidity buffer by continuous mixing at same temperature until a homogenous mixture is formed,
(b) adding aqueous phase containing penetration enhancer and humectant to step (a) with continuous mixing until small transferosomes are formed with complete drug entrapment in side and the resultant formulation is subjected for homogenization or Sonication for further size reduction, and
(c) adding pre-swollen thickening agent or other gelling agent to step (b) and upon uniform mixing, adjusting pH with pH adjusting and volume is made to batch size.

In yet another objective of the present invention is to provide process for the preparation of topical formulations of Rhein or Diacerein in the form of ointment, cream, gel and transferosomal gel which are used to relieve osteoarthritis and inflammation by topical application.

SUMMARY OF INVENTION

Accordingly, the present invention provides a process for the preparation of topical formulations of anthraquinone compound.

In one embodiment, the present invention provides process for the preparation of topical formulations of anthraquinone compound in the form of ointment, cream, gel and transferosomal gel.

In one embodiment, the present invention provides process for the preparation of topical formulations of Rhein or Diacerein as anthraquinone compound.

In one embodiment, the present invention provides process for the preparation of topical formulations of Rhein or Diacerein in the form of ointment, cream, gel and transferosomal gel.

In another embodiment, the present invention provides process for the preparation of topical formulations of Rhein or Diacerein in the form of ointment, cream and gel comprising the steps of heating, adding, stirring, dissolving and mixing.

In yet another embodiment, the present invention provides process for the preparation of topical formulations of Rhein or Diacerein in the form of transferosomal gel comprising the steps of thin film formation, hydration of thin film and transferosomal gel formation.

In yet another embodiment, the present invention provides process for the preparation of topical formulations of anthraquinone compound in the form of ointment or cream or gel, wherein the process comprising the steps of:

a) providing a solution of anthraquinone compound,
b) adding other excipients selected from penetration enhancer, ointment base, humectant, preservatives, emulsifying agent, oil phase vehicle and thickening agent,
c) adjusting the pH of the medium with pH adjusting agent, and
d) adding water and mixing to form ointment or cream or gel of anthraquinone compound.

In yet another embodiment, the present invention provides process for preparing topical formulation in the form of ointment, wherein the process comprising the steps of:

a) heating solvent upto temperature in the range of 45° C. to 55° C. and adding anthraquinone compound slowly with continuous stirring until it is solubilised completely,
b) adding humectant to step a) under continuous stirring and mixing it until homogeneous solution is formed,
c) adding slowly ointment base to step b) under stirring until the solution is mixed homogeneously,
d) dissolving preservatives in small quantity of water and adding to step c), and
e) adding sufficient quantity of purified water and mixing the mixture until ointment is formed.

In yet another embodiment, the present invention provides process for preparing topical formulation in the form of cream, wherein the process comprising the steps of:

a) heating solvent upto temperature in the range of 45° C. to 55° C. and adding anthraquinone compound slowly with continuous stirring until it is solubilised completely,
b) adding emulsifying agent, thickening agent and oil phase vehicle to step a) and mixing it until homogeneous solution is formed,
c) heating portion of water at temperature 80° C. and dissolving preservatives in water,
d) adding humectant, emulsifying agent to step c) under stirring until dissolves, adjusting the pH of the medium with pH adjusting agent,
e) adding slowly the obtained mixture of step d) to step b) under continuous stirring at room temperature, and
f) adding sufficient quantity of purified water and mixing the mixture until cream is formed.

In yet another embodiment, the present invention provides process for preparing topical formulations in the form of gel, wherein the process comprising the steps of:

a) heating solvent upto temperature in the range of 45° C. to 55° C. and adding anthraquinone compound slowly with continuous stirring until the active ingredient is solubilised completely,
b) adding penetration enhancer and humectant by maintaining the temperature at 45° C. to 55° C.,
c) adding thickening agent to step (b) slowly under stirring and some portion of water (about 40-60%) is added intermittently upon maintaining the temperature at 45° C. to 55° C.,
d) dissolving preservatives in small portion of water (about 20-40%) and adding obtained solution to step (c),
e) adjusting the pH of formulation to alkaline pH with a base, and
f) adding quantity sufficient of purified water and mixing the medium until homogeneous gel is formed.

In another embodiment, the present invention provides process for the preparation of topical formulations of anthraquinone compound in the form of transferosomal gel, wherein the process comprising the steps of:

a) thin film formation: dissolving vesicle forming lipid, surfactant and fluidity buffer in organic solvent, dissolving 60% of anthraquinone compound in obtained organic solvent mixture, evaporating organic phase to get thin film,
b) hydration of thin film: dissolving remaining 40% of anthraquinone compound in phosphate buffer (pH 7.4), dissolving preservatives in the obtained anthraquinone compound solution, adding formed aqueous phase to the thin film obtained in step a) and subjecting to rotary flash evaporator to form transferosomes (vesicular systems), sonicating to get uniform unilamellar vesicles, and
c) transferosomal gel: adding thickening agent to the obtained vesicles of step b) and adjusting the pH with triethanolamine to 4.0-6.0 to form viscous gel of anthraquinone compound.

In another embodiment, the present invention provides process for the preparation of topical formulations of anthraquinone compound in the form of transferosomal gel, wherein the process comprising the steps of:

(a) dissolving anthraquinone compound in molten surfactant at 60° C., adding other vesicle forming lipid component and fluidity buffer by continuous mixing at same temperature until a homogenous mixture is formed.
(b) adding aqueous phase containing penetration enhancer and humectant to step (a) with continuous mixing until small transferosomes are formed with complete drug entrapment in side and the resultant formulation is subjected for homogenization or Sonication for further size reduction, and
(c) adding pre-swollen carbomer or other gelling agent to step (b) and upon uniform mixing, adjusting pH with pH adjusting and volume is made to batch size.

In yet another embodiment, the present invention provides process for preparing topical formulation of Rhein or Diacerein in the form of ointment, wherein the process comprising the steps of:

a) heating dimethyl sulfoxide upto temperature in the range of 45° C. to 55° C. and adding Rhein or Diacerein slowly with continuous stirring until it is solubilised completely,
b) adding propylene glycol to step a) under continuous stirring and mixing it until homogeneous solution is formed,
c) adding slowly PEG 400 to step b) under stirring until the solution is mixed homogeneously,
d) dissolving methyl paraben and propyl paraben in small quantity of water and adding to step c), and
e) adding sufficient quantity of purified water and mixing the medium until ointment is formed.

In yet another embodiment, the present invention provides process for preparing topical formulation of Rhein or Diacerein in the form of cream, wherein the process comprising the steps of:

a) heating dimethyl sulfoxide upto temperature in the range of 45° C. to 55° C. and adding Rhein or Diacerein slowly with continuous stirring until solubilised completely,
b) adding span-60, stearic acid and castor oil to step a) and mixing until homogeneous solution is formed,
c) heating portion of water at temperature 80° C. and dissolving methyl paraben and propyl paraben,
d) adding glycerol, Tween-80 to step c) under stirring until dissolves, adjusting the pH of the medium with citric acid monohydrate,
e) adding slowly the obtained mixture of step d) to step b) under continuous stirring at room temperature, and
f) adding sufficient quantity of purified water and mixing the medium until cream is formed.

In yet another embodiment, the present invention provides process for preparing topical formulation of Rhein or Diacerein in the form of gel, wherein the process comprising the steps of:

a) heating dimethyl sulfoxide upto temperature in the range of 45° C. to 55° C. and adding Rhein or Diacerein slowly with continuous stirring until solubilised completely,
b) adding diethylene glycol monoethyl ether and glycerol by maintaining the temperature at 45° C. to 55° C.,
c) adding carbomer to step (b) slowly under stirring and some portion of water (about 40-60%) is added intermittently upon maintaining the temperature at 45° C. to 55° C.,
d) dissolving methyl paraben and propyl paraben in small portion of water (about 20-40%) and adding obtained solution to step (c),
e) adjusting the pH of formulation to alkaline pH with triethanolamine, and
f) adding quantity sufficient of purified water and mixing the mixture until homogeneous gel of Rhein or Diacerein is formed.

In another embodiment, the present invention provides process for the preparation of topical formulations of Rhein or Diacerein in the form of transferosomal gel, wherein the process comprising the steps of:

a) thin film formation: dissolving lecithin, span 60 and cholesterol in organic solvent containing 70:30 parts of dichloromethane and methanol, dissolving 60% of Rhein or Diacerein in obtained organic solvent mixture, evaporating organic phase at 30° C. under reduced pressure by transferring into round bottom flask to get thin film,
b) hydration of thin film: dissolving remaining 40% of Rhein or Diacerein in phosphate buffer (pH 7.4), dissolving methyl paraben and propyl paraben in the obtained Rhein or Diacerein solution, adding formed aqueous phase to the thin film obtained in step a) and subjecting to rotary flash evaporator to form transferosomes (vesicular systems), sonicating to get uniform unilamellar vesicles, and
c) transferosomal gel: adding carbomer to the obtained Rhein or Diacerein vesicles of step b) and adjusting the pH with triethanolamine to 4.0-6.0 to form viscous gel of Rhein or Diacerein.

In another embodiment, the present invention provides process for the preparation of topical formulations of Rhein or Diacerein in the form of transferosomal gel, wherein the process comprising the steps of:

(a) dissolving Rhein or Diacerein in molten span-60 at 60° C., adding Lecithin and cholesterol by continuous mixing at same temperature until a homogenous mixture is formed,
(b) adding Transcutol-P and glycerol to step (a) with continuous mixing until small transferosomes are formed with complete drug entrapment in side and the resultant formulation is subjected for homogenization or Sonication for further size reduction, and
(c) adding pre-swollen Carbopol or other gelling agent to step (b) and upon uniform mixing, adjusting pH with triethanolamine and volume is made to batch size.

DETAILED DESCRIPTION OF THE INVENTION

Figure 1:
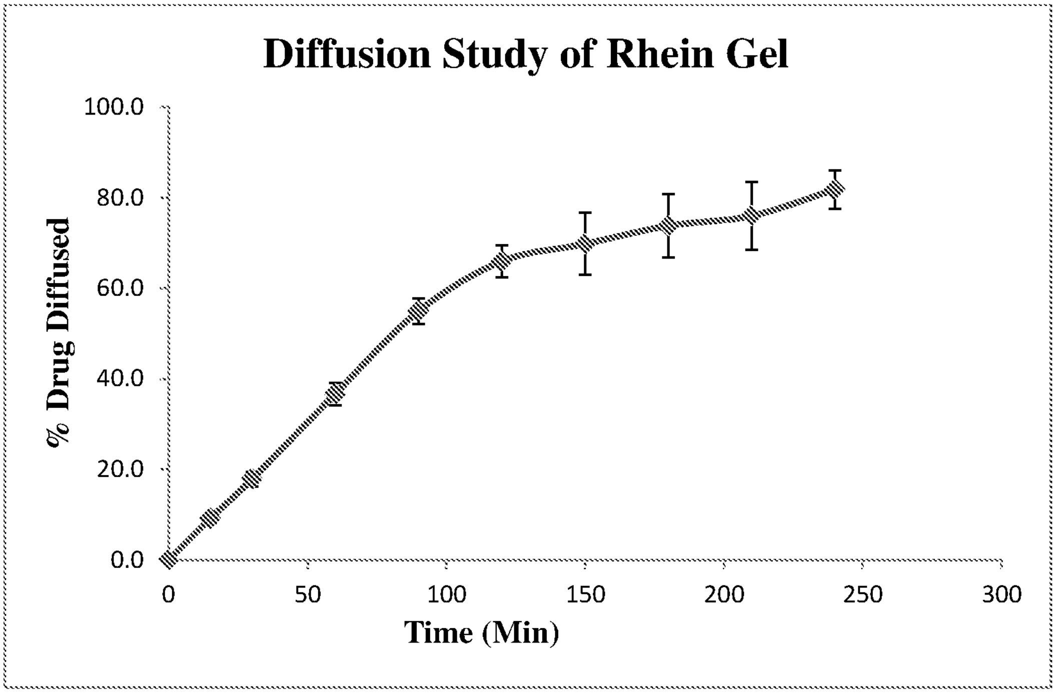
FIG. 1 shows the percentage of drug diffusion of Rhein gel according to Example 3.

The term "comprising", which is synonymous with "including", "containing", or "characterized by" here is defined as being inclusive or open-ended, and does not exclude additional, unrecited elements or method steps, unless the context clearly requires otherwise.

The present invention provides process for the preparation of topical formulations of anthraquinone compound.

The present invention provides process for the preparation of topical formulations of Rhein or Diacerein as anthraquinone compound.

The present invention provides process for the preparation of topical formulations of Rhein or Diacerein in the form of ointment, cream, gel and transferosomal gel.

The present invention provides process for the preparation of topical formulations of Rhein or Diacerein in the form of ointment, cream and gel comprising the steps of heating, adding, stirring, dissolving and mixing and transferosomal gel comprising the steps of thin film formation, hydration of thin film and transferosomal gel formation.

The present invention provides process for the preparation of topical formulations of anthraquinone compound in the form of ointment or cream or gel comprising the steps of providing a solution of anthraquinone compound, adding other excipients selected from penetration enhancer, ointment base, humectant, preservatives, emulsifying agent, oil phase vehicle and thickening agent, adjusting the pH of the medium with pH adjusting agent, adding water and mixing to form ointment or cream or gel.

The term "active ingredient" of the present invention is used to relieve osteoarthritis and inflammation. Preferably used active ingredient is anthraquinone compound. Most preferably used active ingredient is Rhein or Diacerein.

Rhein (4,5-dihydroxyanthraquinone-2-carboxylic acid), the active component of Rhubarb, has been shown to have multiple functions, such as antibacterial, anti-oxidant, anti-cancer, anti-angiogenic, anti-inflammatory effects and also used in treatment of osteoarthritis.

Rhein is the main effective ingredient isolated from *Rheum palmatum* L. Radix et Rhizoma. It is the dried root and rhizome of *R. palmatum* L., *R. tanguticum* Maxim. ex Balf., or *R. officinale* Baill. of the family Polygonaceae, whose major active constituents are anthraquinone derivatives. The root bark of rhein belongs to the Ranunculaceae family.

Diacerein (4,5-diacetoxy-9,10-dihydro-9,10-dioxo-2 anthracene carboxylic acid) is a purified anthraquinone that is entirely transformed during absorption into rhein, the active metabolite found in plasma and synovial fluid. It belongs to a new class of anti-osteoarthritis drugs, known as "disease modifying osteoarthritis drugs (DMOAD)" or "chondroprotective agents". For its actions both in vivo and in vitro, Diacerein has been used in the treatment of osteoarthritis and demonstrated benefits in alleviating joint pain in humans and in rodent models of the disease.

Diacerein is the di-acetylated derivative of rhein and lacks cyclooxygenase inhibitory activity therefore having no effect on prostaglandin synthesis. It is a selective inhibitor of interleukin-1 having protective effect on granuloma-induced cartilage breakdown by a reduction in the concentrations of proinflammatory cytokines.

The transfersome term was first introduced by Cevc (Transfersomes, a trademark of IDEA AG, Munich, Germany), and it represents the first generation of ultradeformable vesicles. The skin permeation and penetration of these elastic vesicles result from a synergic mechanism among the carrier properties and the access enrichment ability. Transfersomes are ultradeformable lipid bundles of aggregates in supramolecular form constructed with a minimum of one interior aqueous segment encircled by a lipid bilayer exhibiting adapted properties, which are appropriate under the presence of surfactants in the vesicular membrane (edge activator (EA)). Even if it is generally accepted that the permeation of, usually, liposomes is limited to the outer layer of the stratum corneum, thus providing a drug or cosmetic localizing effect within the skin, transfersomes are claimed to infuse as intact vesicles through the skin layers to the complete circulation.

The term "solvent" of the present invention includes but not limited topolyols and polyglycols such as propylene glycol (1,2-propanediol), glycerin (glycerol), glycol furol, 1,2-phenol-hexanetriol, sorbitol solution, esters and polyesters such as polyoxyethylene sorbitan monoesters (e.g., Tween® 60) and polyoxy ethylene sorbitan polyesters (e.g., Tween® 20), ethers and polyethers such as polyethylene glycol monocetyl ether (cetomacrogol 1000) and polyethylene-polypropylene glycols (pluronics), dimethyl sulfoxide, alcohol, castor oil, diisopropyl adipate, ethoxylated alcohol, ethyl alcohol, fatty alcohol citrate, glycerin, 1,2,6-hexanetriol, hexylene glycol, isopropyl alcohol, isopropyl myristate, isopropyl palmitate, mineral oil, phosphoric acid, polyethylene glycol 300, polyethylene glycol 400, polyethylene glycol 1450, polyethylene glycol 8000, polyethylene glycol monostearate, polyethylene glycol 400 monostearate, polyethylene glycols, polyoxyl 20 cetostearyl ether, polyoxypropylene 15-stearyl ether, polysorbate 20, polysorbate 40, polysorbate 60, polysorbate 80, polysorbates, propylene carbonate, purified water, SD alcohol 40, triglycerides of saturated fatty acids. Preferably used solvent is dimethyl sulfoxide.

The term "ointment base" of the present invention includes four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight. Preferably used ointment base is PEG 4000.

Humectant includes but not limited to glycerol, sorbitol, maltitol, polydextrose, triacetin, propylene glycol, polyethylene glycol (PEG) esters including PEG-20 stearate, PEG-40 stearate, PEG-150 stearate, PEG-150 distearate and PEG-100 stearate, alkoxylated alcohols including laureth-12, ceteareth-20, laureth-23, glycereth-7, glycereth-12, glycereth-26, PEG-4, PEG-6, PEG-8, PEG-12, PEG-32, PEG-75, PEG-150, dipropylene glycol, polypropylene glycol, pantothenol, gluconic acid salts. Preferably used humectants are glycerol and propylene glycol.

The term "preservatives" of the present invention includes but not limited tomethyl paraben, propyl paraben, chlorocresol, sorbic acid, potassium sorbatesodium benzoate, phenoxyethanol, benzyl alcohol, imidazolidinyl urea, or diazolidinyl urea butylated hydroxy toluene, butylated hydroxyanisole, ethylenediamine tetraacetic acid, paraoxybenzoic acid esters, chlorobutanol, phenylethyl alcohol, dehydroacetic acid, sorbic acid, benzalkonium chloride, benzethonium chloride, phenol, phenylmercuric nitrate, Thimerosal. Preferably used preservatives are methyl paraben and propyl paraben.

The term "emulsifying agent" or "surfactant" of the present invention includes but not limited to polawax, polysorbate 20, polysorbate 40, polysorbate 60, polysorbate 80, Span 60. Polysorbates are a series of partial fatty acid esters of sorbitol and its anhydrides copolymerized with approximately 20, 5 or 4 moles of ethylene oxide for each mole of sorbitol and its anhydrides. Polysorbates may function as an emulsifying agent or solubilizing agent. "Span 60" refers to sorbitan monostearate and is a series of mixtures of partial esters of sorbitol and mono- or di-anhydrides with fatty acids. Preferably used emulsifying agents or surfactants are Span-60 and Tween-80 or polysorbate 80.

The term "thickening agent" of the present invention includes but not limited to natural or synthetic polymeric carbohydrate (e.g., cellulose, pharmaceutically acceptable vegetable gums); a polymeric or oligomeric derivative of a polymeric carbohydrate that is produced by chemical modification (e.g., hydroxypropyl cellulose, hydroxypropyl methyl cellulose, hydroxyethyl cellulose); or mixtures thereof. Representative cellulosic thickening agents include cellulose, hydroxypropyl cellulose ("HPC"), hydroxypropyl methyl cellulose, hydroxyethyl cellulose, methyl cellulose, acacia, alginic acid bentonite, polyvinyl pyrrolidone, magnesium aluminium silicate, carbomer, microcrystalline cellulose, carboxymethylcellulose calcium or sodium, cetostearyl alcohol, ethylcellulose, glycerin, gelatin, guar gum, hydroxypropyl cellulose, maltodextrin, polyvinyl alcohol, povidone, propylene carbonate, propylene glycol alginate, sodium alginate, sodium starch glycolate, starch, tragacanth, stearic acid and xanthan gum. Preferably used thickening agents are stearic acid and carbomer.

The term "oil phase vehicle" of the present invention includes but not limited to vegetable oil, a mineral oil, a medium chain triglyceride (MCT) oil, i.e., a triglyceride oil in which the carbohydrate chain has 8-12 carbons, or a combination of two or three of such oils. MCT includes MCT oils include TCR (trade name of Societe Industrielle des Oleagineaux, France for a mixture of triglycerides wherein about 95% of the fatty acid chains have 8 or 10 carbons) and MIGLYOL 810 or 812 (trade name of Dynamit Nobel, Sweden for a mixed triester of glycerine and of caprylic and capric acids). Vegetable oils include soybean oil, cotton seed oil, olive oil, sesame oil and castor oil. The mineral oils may be natural hydrocarbons or their synthetic analogs. Preferably used oil phase vehicle is castor oil.

The term "pH adjusting agent" of the present invention includes but not limited to triethanolamine (TEA), citric acid monohydrate, amine base tromethamine, tetrahydroxypropyl ethylenediamine, diethanolamine, aminomethyl propanol, and/or sodium or ammonium hydroxide. Preferably used pH adjusting agents are citric acid monohydrate and triethanolamine.

The term "penetration enhancer" of the present invention includes but not limited to propylene glycol, glycerine, isopropyl palmitate, isopropyl myristate, laurocapram, oleic acid, oleyl alcohol, ethoxydiglycol, alkanecarboxylic acids, Azone®, adipic acid derivatives, ethanol, urea, polyethylene glycol (PEG), dimethylsulfoxide (DMSO), polar lipids, or N-methyl-2-pyrrolidone, diethylene glycol monoethyl ether, calcipotriene, detergents, emollients, ethoxy diglycol, triacetin, benzyl alcohol, sodium laureth sulfate, dimethyl isosorbide, isopropyl myristate, medium chain triglyceride oil (MCT Oil), menthol, isopropyl isostearate, propylene glycol monostearate, lecithin, diisopropyl adipate, diethyl sebacate, oleic acid, ethyl oleate, glyceryl oleate, caprylic/capric triglyceride, propylene glycol dicaprylate/dicaprate, laureth 4, oleth-2, oleth-20, propylene carbonate, nonoxynol-9,2-n-nonyl-1,3-dioxolane, $C_7$ to $C_{14}$-hydrocarbyl substituted 1,3-dioxolane, 1,3-dioxane, or acetal and nonoxynol-15. Preferably used penetration enhancer is diethylene glycol monoethyl ether.

Vesicle forming lipid is a phospholipid. Any naturally occurring or synthetic phospholipid can be used. Without limitation, examples of specific phospholipids are, soya lecithin, L-a-(distearoyl) lecithin, L-a-(diapalmitoyl) lecithin, L-a-phosphatide acid, L-a-(dilauroyl)-phosphatidic acid, L-a (dimyristoyl) phosphatidic acid, L-a(dioleoyl) phosphatidic acid, DL-a(dipalmitoyl) phosphatidic acid, L-a (distearoyl) phosphatidic acid, and the various types of L-a-phosphatidylcholines prepared from egg yolk, soybean and the like, or synthetically, and salts thereof. Preferably used vesicle forming lipid is soya lecithin.

Cholesterol acts as a "fluidity buffer" at higher and lower temperatures and prevents the collapse of the plasma membrane during thermical pressures. Cholesterol-rich domains in the bilayer are called lipid rafts.

The following examples describes the nature of the invention and are given only for the purpose of illustrating the present invention in more detail and are not limitative and relate to solutions, which have been particularly effective on bench scale and prepared by the process of the present invention.

Example 1

Composition of Rhein Ointment

| Ingredients | mg/gm | % w/w |
|---|---|---|
| Rhein | 10.0 | 1% |
| Dimethyl Sulfoxide | 450.0 | 45% |
| PEG 4000 | 300.0 | 30% |
| Propylene glycol | 200.0 | 20% |
| Methyl paraben | 1.00 | 0.10% |
| Propyl paraben | 0.20 | 0.02% |
| Purified Water | 38.80 | 3.88% |
| Total Weight | 1000.00 | 100% |

Manufacturing Process

DMSO is heated up to 45° C. to 55° C. and Rhein is added slowly with continuous stirring until it is solubilised completely. Propylene glycol was added to the formed solution under continuous stirring and mixed until a homogeneous solution is formed. PEG-4000 was added to the obtained solution slowly under stirring until it is mixed homogeneously. Methyl paraben and propyl paraben were dissolved in small quantity of water and added to obtained solution. Sufficient quantity of purified water is added and mixed until Rhein ointment is formed.

Example 2

Composition of Rhein Cream

| Ingredients | mg/gm | % w/w |
|---|---|---|
| Phase-I | | |
| Rhein | 10.0 | 1% |
| Dimethyl Sulfoxide | 450.0 | 45% |
| Span - 60 | 20.0 | 2% |
| Stearic acid | 80.0 | 8% |
| Castor Oil | 150.00 | 15% |
| Phase-II | | |
| Tween-80 | 10.00 | 1% |
| Glycerol | 30.00 | 3.00% |
| Citric acid monohydrate | 2.00 | 0.2% |
| Methylparaben | 1.00 | 0.10% |
| Propylparaben | 0.20 | 0.02% |
| Purified Water | 246.80 | 24.68% |
| Total Weight | 1000.00 | 100% |

Manufacturing Process

DMSO is heated up to 45° C. to 55° C. and Rhein is added slowly with continuous stirring until it is solubilised completely. Span-60, stearic acid and castor oil were added to above drug solution and mixed until homogeneous solution is formed. A portion of purified water was heated to 80° C. and methyl paraben and propyl paraben were dissolved in it. Then Glycerol, Tween-80 and citric acid were added to it and stirred continuously until dissolved. Obtained mixture is added to previously formed homogeneous solution under continuous stirring at room temperature. Sufficient quantity of purified water is added and mixed until Rhein cream is formed.

Example 3

| Composition of Rhein Gel | | |
|---|---|---|
| Ingredients | mg/gm | % w/w |
| Rhein | 10.0 | 1% |
| Dimethyl Sulfoxide | 450.0 | 45% |
| Diethylene glycol monoethyl ether | 50.0 | 5% |
| Glycerol | 100.0 | 10% |
| Carbomer | 10.0 | 1% |
| Triethanolamine | 0.76 | 0.076% |
| Methyl paraben | 1.00 | 0.1% |
| Propyl paraben | 0.20 | 0.02% |
| Purified Water | 378.04 | 37.8% |
| Total Weight | 1000.00 | 100% |

Manufacturing Process

DMSO is heated up to 45° C. to 55° C. and Rhein is added slowly with continuous stirring until it is solubilised completely. Then diethylene glycol monoethyl ether & glycerol were added by maintaining the temperature at 45° C. to 55° C. Carbomer is added slowly under stirring and some portion of water (about 40-60%) is added intermittently upon maintaining the temperature at 45° C. to 55° C. Methyl paraben and propyl paraben were dissolved in small portion of water (about 20-40%) and added to obtained solution. pH of the formulation is adjusted to alkaline pH with triethanolamine, sufficient quantity of purified water is added and mixed until Rhein gel is formed. The percentage of drug diffusion of Rhein gel is shown in FIG. 1.

| Evaluation tests for Rhein gel: | |
|---|---|
| pH | 4.48 |
| Viscosity @ 100 RPM, cPs | 1972.1 |
| Assay (%) | 103.23 |

| Diffusion Results | |
|---|---|
| Time, hrs | % Drug Release |
| 0.25 | 0.00 |
| 0.5 | 3.59 |
| 0.75 | 12.23 |
| 1 | 25.14 |
| 1.5 | 47.97 |
| 2 | 70.50 |
| 3 | 90.31 |
| 4 | 103.05 |

The percentage of drug release of Rhein gel Vs time is given in FIG. 1.

Example 4

| Composition of Rhein Gel | | |
|---|---|---|
| Ingredients | mg/gm | % w/w |
| Rhein | 10.00 | 1% |
| Dimethylsulphoxide (DMSO) | 450.00 | 45% |
| Diethylene glycol monoethylether (Transcutol-P) | 50.00 | 5% |
| Glycerol | 100.0 | 10% |
| Carbopol (Acrypol - 956) | 10.00 | 1% |
| Triethanolamine | 0.76 | 0.076% |
| Purified water | 379.24 | 37.9% |
| Total Weight | 1000.00 | 100% |

Manufacturing Process

Rhein was added to preheated Dimethylsulphoxide (DMSO) at 45-55° C. and stirred until Rhein was dissolved. Transcutol-P and glycerol were added and stirred for about 10 mins under continuous heating. Carbomer (acrypol) was added slowly and stirred continuously by maintaining 45-55° C. with intermittent addition of purified water. Remaining amount of water was added and mixed continuously for about 2 hours until uniform gel is formed. Triethanolamine was added to adjust the pH and to impart gelling nature to the product and mixed vigorously for 15 mins. The final product was packed carefully in a tight, light-resistant containers.

Example 5

| Composition of Rhein Transferosomal Gel | | |
|---|---|---|
| Ingredients | mg/gm | % w/w |
| Rhein | 3.0 | 0.3 |
| Soya Lecithin | 10.0 | 1 |
| Span-60 | 75.0 | 7.5 |
| Cholesterol | 20.0 | 2 |
| Methyl Paraben | 1 | 0.1 |
| Propyl Paraben | 0.20 | 0.02 |
| Carbomer | 0.75 | 0.075 |
| pH 7.4 PBS | 880.45 | 88.045 |
| Triethanolamine | 0.35 | 0.035 |
| Dichloromethane | 1.82 | 0.182 |
| Methanol | 0.78 | 0.078 |
| Total Weight | 1000.00 | 100 |

Manufacturing Process

1. Thin film formation:

Leicithin, span 60 and cholesterol were dissolved in organic solvent containing 70:30 parts of dichloromethane and methanol. 60% of API was dissolved in above organic solvent mixture. This organic phase was transferred to round bottom flask of rotary flash evaporator and evaporated to form thin film at 30° C. under reduced pressure.

2. Hydration of thin film:

Remaining 40% of rhein was dissolved in 7.4 pH phosphate buffer. Methyl paraben and propyl paraben were dissolved in above drug solution. This aqueous phase is added to thin film formed above to form the transferosomes (vesicular systems). Transferosomes are collected from rotary flash evaporator and sonicated for 30 minutes to form uniform unilamellar vesicles.

3. Transferosomal Gel

Carbomer is added to the above formed rhein containing transferosomes and pH is adjusted with triethanolamine to 4.0-6.0 to form the viscous Transferosomal gel of Rhein.

Figure 2:
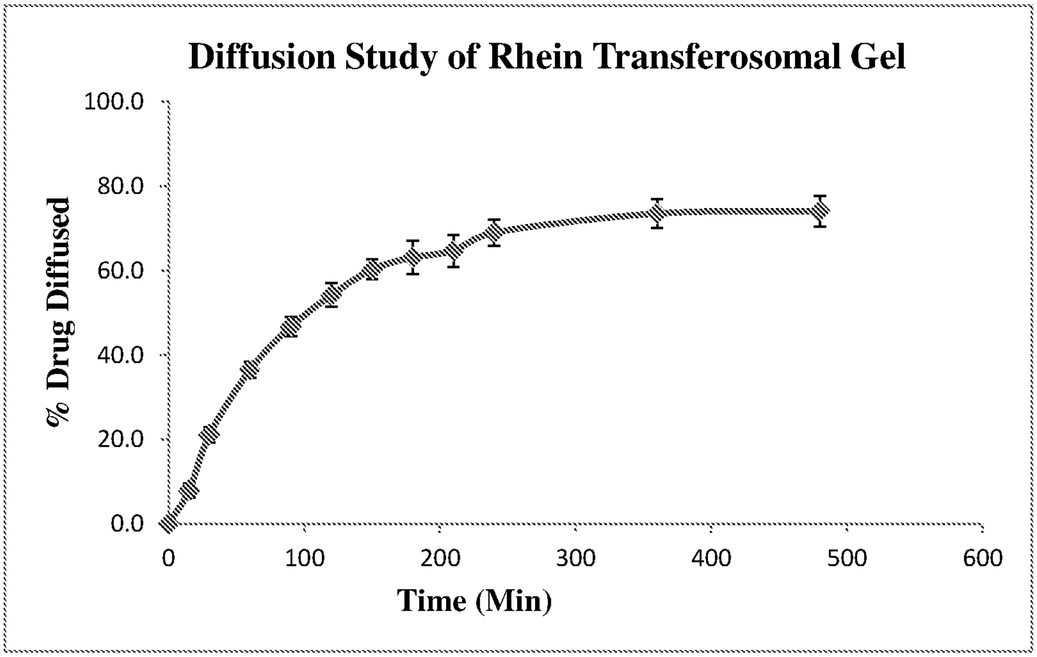
FIG. 2 shows the percentage of drug diffusion of Rhein transferosomal gel according to Example 4.

The percentage of drug diffusion of Rhein transferosomal gel is shown in FIG. 2.

Example 6

| Composition of Rhein Transferosomal Gel | | |
|---|---|---|
| Ingredients | mg/gm | % w/w |
| Rhein | 10.00 | 1 |
| Lecithin | 10.00 | 1 |
| Cholesterol | 20.00 | 2 |
| Span-60 | 75.00 | 7.5 |
| Transcutol-P | 50.00 | 5 |
| Glycerol | 100.00 | 10 |
| Carbopol (Acrypol - 956) | 5.00 | 0.5 |
| Triethanolamine | 0.80 | 0.080 |
| pH 7.4 Phosphate buffer | 729.2 | 72.92 |
| Total Weight | 1000 | 100 |

Manufacturing Process

Span-60 was added to 80% quantity of pH 7.4 phosphate buffer and stirred at 50-60° C. Rhein was added and mixed for 1 hour at 50-60° C. until dissolved. Lecithin and cholesterol were added to the obtained mixture and mixed for 3 hours at 50-60° C. until dissolved. Transcutol and glycerol were added and stirred for 2 hours until small transfer-osomes are formed with complete drug entrapment in side and the resultant formulation is subjected for homogenization or Sonication for further size reduction. Carbomer was slowly added and stirred continuously until completely swelled and volume was made up with remaining portion of pH 7.4 phosphate buffer. Triethanolamine was added and stirred continuously until a uniform and consistent gel was formed.

Example 7

| Composition of Rhein Transferosomal gel | | |
|---|---|---|
| Ingredients | mg/gm | % w/w |
| Rhein | 3.00 | 0.3 |
| Lecithin | 10.00 | 1 |
| Cholesterol | 20.00 | 2 |
| Span - 60 | 75.00 | 7.5 |
| Methylparaben | 1.00 | 0.1 |
| Propylparaben | 0.20 | 0.02 |
| Carbopol (Acrypol - 956) | 7.50 | 0.75 |
| Dichloromethane | 2.8 mL | 0.28 |
| Methanol | 1.2 mL | 0.12 |
| Triethanolamine | 0.35 | 0.035 |
| pH 7.4 Phosphate buffer | 878.95 | 87.89 |
| Total Weight | 1000 | 100 |

Manufacturing Process

Lecithin, cholesterol and span-60 were allowed to dissolve in organic solvent mixture (dichloromethane:methanol) and a portion of Rhein was added and sonicated for 30 mins and then the solvents were evaporated using a rotary evaporator at 45° C. at 90 rpm for 45 min. Portion of pH 7.4 phosphate buffer was heated up to 70° C. and methylparaben and propylparaben were added separately and cooled to room temperature, remaining portion of Rhein was added and sonicated for 30 min. Obtained mixtures were stirred continuously using rotary evaporator at 45° C. at 150 rpm for 60 min. Resultant mixture was collected into beaker, kept aside for 120 min and sonicated for 30 min and was made up to the weight using pH 7.4 phosphate buffer. Carbomer was slowly added and stirred continuously. Triethanolamine was added and stirred continuously until a uniform and consistent gel was formed.

Example 8

| Composition of Rhein Transferosomal gel | | |
|---|---|---|
| Ingredients | mg/gm | % w/w |
| Rhein | 3.00 | 0.3 |
| Lecithin | 10.00 | 1 |
| Cholesterol | 20.00 | 2 |
| Span - 60 | 75.00 | 7.5 |
| Methylparaben | 1.00 | 0.1 |
| Propylparaben | 0.20 | 0.02 |
| Carbopol (Acrypol - 956) | 5.00 | 0.5 |
| Dichloromethane | 2.8 mL | 0.28 |
| Methanol | 1.2 mL | 0.12 |
| Triethanolamine | 0.35 | 0.035 |
| pH 7.4 Phosphate buffer | 881.45 | 88.14 |
| Total Weight | 1000 | 100 |

Manufacturing Process

Lecithin, cholesterol and span-60 were allowed to dissolve in organic solvent mixture (dichloromethane:methanol) and a portion of Rhein was added and sonicated for 30 mins and then the solvents were evaporated using a rotary evaporator @ 45° C. at 90 rpm for 45 min. A known portion of pH 7.4 phosphate buffer was heated up to 70° C. and to it dispensed quantities of methylparaben and propylparaben were added and cooled to room temperature, followed by addition of remaining portion of Rhein and sonicated for 30 min. Obtained mixture is added to Rhein mixture and continued stirred using rotary evaporator @ 45° C. at 150 rpm for 60 min. Obtained mixture was collected into beaker, kept aside for 120 min and sonicated for 30 min. Carbomer was slowly added and stirred continuously and was made up to the weight using pH 7.4 phosphate buffer. Triethanolamine was added and stirred continuously until a uniform and consistent gel was formed.

Example 9

| Composition of Diacerein Transferosomal Gel | | |
|---|---|---|
| Ingredients | mg/gm | % w/w |
| Diacerein | 10.00 | 1 |
| Lecithin | 10.00 | 1 |
| Cholesterol | 20.00 | 2 |
| Span - 60 | 75.00 | 7.5 |
| Transcutol-P | 50.00 | 5 |
| Glycerol | 100.00 | 10 |
| Carbopol (Acrypol - 956) | 10.00 | 1 |
| Triethanolamine | 5.00 | 0.5 |
| pH 7.4 Phosphate buffer | 720 | 72 |
| Total Weight | 1000 | 100 |

Manufacturing Process

Span-60 was added to 80% quantity of pH 7.4 phosphate buffer and stirred at 50-60° C. Diacerein was added and mixed for 30 min at 50-60° C. until dissolved. Lecithin and cholesterol were added to the obtained mixture and mixed for 1 h at 50-60° C. until dissolved. Transcutol and glycerol were added to obtained mixture and stirred for 15 min until small transferosomes are formed with complete drug entrapment in side and the resultant formulation is subjected for homogenization or Sonication for further size reduction. Carbomer was slowly added to the obtained mixture and stirred continuously until completely swelled and volume was made up with remaining portion of pH 7.4 phosphate buffer. Triethanolamine was added to the obtained mixture and stirred continuously until a uniform and consistent gel was formed.

Example 10

Composition of Diacerein Transferosomal Gel

| Ingredients | mg/gm | % w/w |
|---|---|---|
| Diacerein | 10.00 | 1 |
| Lecithin | 10.00 | 1 |
| Cholesterol | 20.00 | 2 |
| Span - 60 | 75.00 | 7.5 |
| Transcutol-P | 50.00 | 5 |
| Glycerol | 100.00 | 10 |
| Carbopol (Acrypol - 956) | 5.00 | 0.5 |
| Triethanolamine | 0.80 | 0.080 |
| pH 7.4 Phosphate buffer | 729.2 | 72.92 |
| Total Weight | 1000 | 100 |

Manufacturing Process

Span-60 was added to 80% quantity of pH 7.4 phosphate buffer and stirred at 50-60° C. Diacerein was added and mixed for 60 min at 50-60° C. until dissolved. Lecithin and cholesterol were added and mixed for 3 h at 50-60° C. until dissolved. Transcutol and glycerol were added and stirred for 2 h until small transferosomes are formed with complete drug entrapment in side and the resultant formulation is subjected for homogenization or Sonication for further size reduction. Carbomer was slowly added and stirred continuously until completely swelled and volume was made up with remaining portion of pH 7.4 phosphate buffer. Triethanolamine was added and stirred continuously until a uniform and consistent gel was formed.

Physical characteristics of Rhein Gel according to Example 3 are as given below:

| S. No. | Test | Specifications | Results |
|---|---|---|---|
| 1. | Description | A yellow color gel | A yellow color gel |
| 2. | Identification | The infrared absorption spectrum of the sample shall be concordant with that of the infrared absorption spectrum of Rhein Standard | Complies |
| 3. | pH | 4.0 to 6.0 | 5.22 |
| 4. | Viscosity @ 100 rpm, Pa · s | 1.8-3.2 | 1.855 |
| 5. | Diffusion, % | NLT 70% in 240 mins | 71.5 |

Physical characteristics of Rhein Transferosomal Gel according to Example 4 are as given below:

| S. No. | Test | Specifications | Results |
|---|---|---|---|
| 1. | Description | Yellow color gel | Yellow color gel |
| 2. | pH | 4.0 to 6.0 | 4.48 |

Physical characteristics of Rhein Transferosomal Gel according to Example 6 are as given below:

| S. No. | Test | Specifications | Results |
|---|---|---|---|
| 3. | Description | A yellow color gel | A yellow color gel |
| 4. | Identification | The infrared absorption spectrum of the sample shall be concordant with that of the infrared absorption spectrum of Rhein Standard | Complies |
| 5. | pH | 4.5 to 6.5 | 5.94 |
| 6. | Assay, % | NLT 90%-NMT 110% | 97.2 |
| 7. | Diffusion % | NLT 70% in 480 mins | 66.70 |

Physical characteristics of Rhein Transferosomal Gel according to Example 7 are as given below:

| S. No. | Test | Specifications | Results |
|---|---|---|---|
| 1. | Description | Yellow color gel | Yellow color gel |
| 2. | pH | 4.5 to 6.5 | 5.36 |
| 3. | Diffusion @ 240 min | NLT 50% | 69.0% |

Physical characteristics of Diacerein Transferosomal Gel according to Example 8 are as given below:

| S. No. | Test | Specifications | Results |
|---|---|---|---|
| 1. | Description | A yellow color gel | A yellow color gel |
| 2. | Identification | The infrared absorption spectrum of the sample shall be concordant with that of the infrared absorption spectrum of Rhein Standard | Complies |
| 3. | pH | 4.5 to 6.5 | 6.15 |
| 4. | Viscosity @ 100 rpm, Pa · s | 1.0 to 2.0 | 1.38 |
| 5. | Assay, % | NLT 90%-NMT 110% | 99.3 |
| 6. | Assay of methylparaben, % | NLT 90%-NMT 110% | 98.6 |
| 7. | Assay of propylparaben, % | NLT 90%-NMT 110% | 90.55 |
| 8. | Diffusion, % | NLT 70% in 480 mins | 75.5% |

Physical characteristics of Diacerein Transferosomal Gel according to Example 9 are as given below:

| S. No. | Test | Specifications | Results |
|---|---|---|---|
| 1. | Description | Yellow color gel | Yellow color gel |
| 2. | pH | 4.5 to 6.5 | 6.35 |
| 3. | Assay of Rhein | NLT 90%-NMT 110% | 90 |
| 4. | Diffusion @ 360 min | NLT 50% | 56.9 |

Physical characteristics of Diacerein Transferosomal Gel according to Example 10 are as given below:

| S. No. | Test | Specifications | Results |
|---|---|---|---|
| 1. | Description | Yellow color gel | Yellow color gel |
| 2. | pH | 4.5 to 6.5 | 5.84 |

In-Vitro Permeability Studies (Skin Permeability Studies)

The assessment of percutaneous permeation is key to the successful development of new formulations intended for human use. More commonly used models to conduct skin-permeation studies are ex vivo human or animal skin. The assessment of percutaneous absorption of molecules is an important step in the evaluation of any topical drug-delivery system or formulation. If the dosage form is to be used in humans, the most relevant skin-absorption data should come from in vivo human studies. However, such studies are generally not feasible during the initial development of a novel pharmaceutical dosage form. Moreover, ex vivo human skin may not be readily available, and so researchers have relied on animal studies for much of the experimental data. This creates a major challenge in correlating results from ex vivo animal experiments with ex vivo and in vivo human studies for prediction of human percutaneous absorption.

A wide range of animal models has been used as alternatives to human skin to evaluate percutaneous permeation of substances. These include pig, mouse, rat, guinea pig, and snake models. Porcine (pig) skin is histologically similar to human skin, with a comparable SC thickness of 21-26 μm. In addition, the average hair-follicle density in porcine ear skin is 20/$cm^2$ compared to 14-32/$cm^2$ in human forehead skin. As well as being similar to human skin, porcine ear skin is also convenient to obtain and has been widely used in skin-permeation studies.

Figure 3:
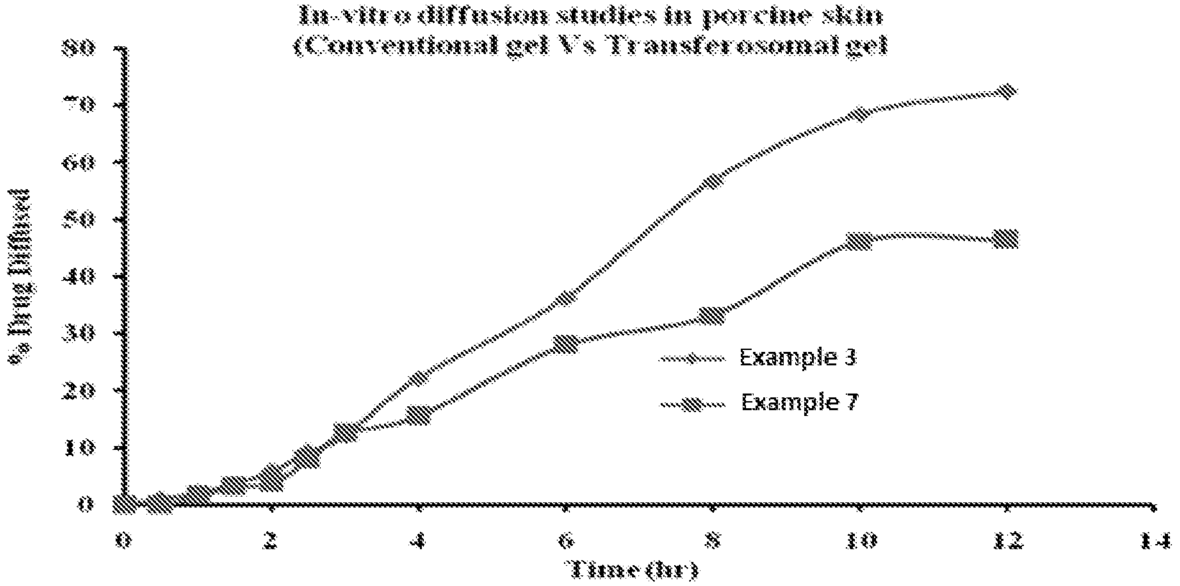
FIG. 3 shows comparison of diffusion studies of Rhein gel according to Example 3 and transferosomal gel according to Example 7 using porcine skin.

Comparison of diffusion studies of Rhein gel according to Example 3 and transferosomal gel according to Example 7 using porcine skin is shown in FIG. 3.

Figure 4:
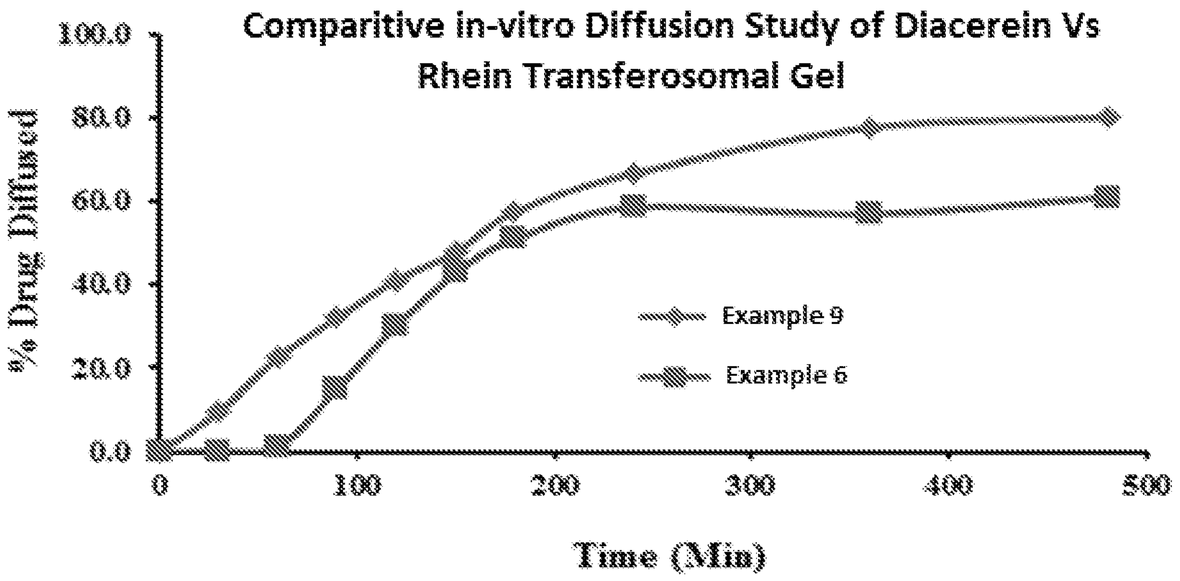
FIG. 4 shows comparison of in-vitro diffusion study of Diacerein Transferosomal Gel according to Example 9 and Rhein Transferosomal gel according to Example 6.

Comparison of in-vitro diffusion study of Diacerein Transferosomal Gel according to Example 9 and Rhein Transferosomal gel according to Example 6 is shown in FIG. 4.

Figure 5:
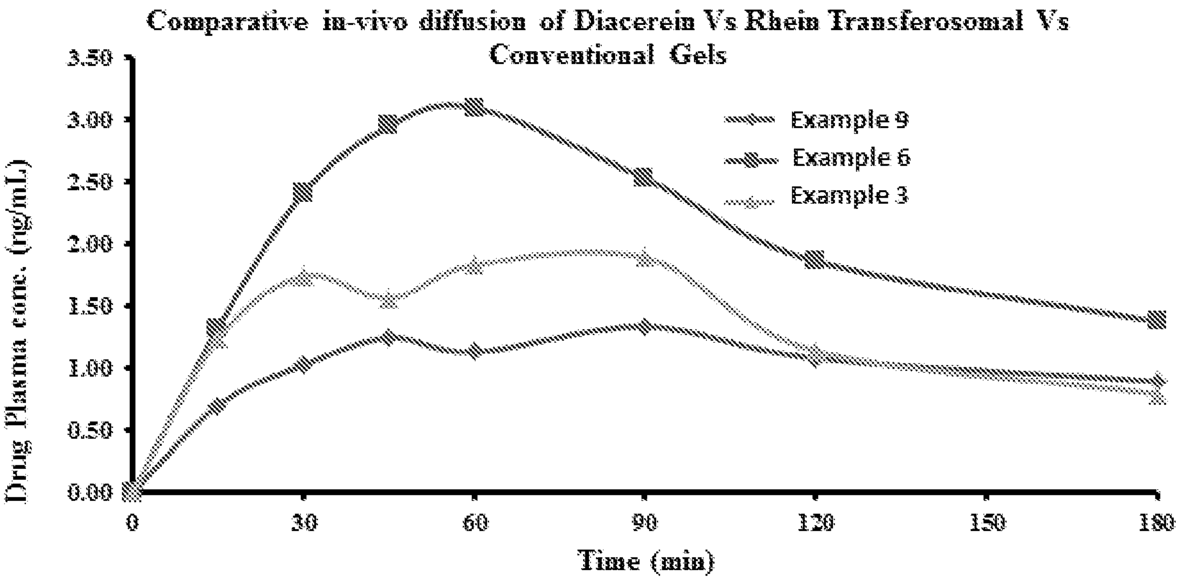
FIG. 5 shows comparison of in-vivo diffusion study of Diacerein Transferosomal Gel according to Example 9, Rhein Transferosomal gel according to Example 6 and Rhein gel according to Example 3.

Comparison of in-vivo diffusion study of Diacerein Transferosomal Gel according to Example 9, Rhein Transferosomal gel according to Example 6 and Rhein gel according to Example 3 is shown in FIG. 5.

We claim:

1. A process for the preparation of rhein transferosomal gel, wherein the process comprises the steps of:

(a) dissolving Rhein in molten surfactant at 60° C., adding a vesicle forming lipid component and a fluidity buffer by continuous mixing at 60° C. until a homogenous mixture is formed, (b) adding an aqueous phase containing a penetration enhancer and a humectant to step (a) with continuous mixing until small transferosomes are formed with complete rhein entrapment and then homogenizing or sonicating to further reduce the size of said transferosomes, and (c) adding a pre-swollen thickening agent or gelling agent to step (b) and mixing, and adjusting pH with a pH adjusting agent.

2. The process for the preparation of Rhein as claimed in claim 1, wherein the Surfactant is selected from polawax, polysorbate 20, polysorbate 40, polysorbate 60, polysorbate 80, or Sorbitan monostearate.

3. The process for the preparation of Rhein as claimed in claim 1, wherein the vesicle forming lipid component is a phospholipid, which is soya lecithin, L-a-(distearoyl) lecithin, L-a-(diapalmitoyl) lecithin, L-a-phosphatide acid, L-a-(dilauroyl)-phosphatidic acid, L-a(dimyristoyl) phosphatidic acid, L-a(dioleoyl) phosphatidic acid, DL-a (dipalmitoyl) phosphatidic acid, L-a(distearoyl) phosphatidic acid, L-a-phosphatidylcholines and salts thereof.

4. The process for the preparation of Rhein as claimed in claim 1, wherein the fluidity buffer is selected from Cholesterol.

5. The process for the preparation of Rhein as claimed in claim 1, wherein the penetration enhancer is selected from propylene glycol; glycerine, isopropyl palmitate, isopropyl myristate, laurocapram, oleic acid, oleyl alcohol, ethoxydiglycol, alkanecarboxylic acids, adipic acid derivatives, ethanol, urea, polyethylene glycol (PEG), dimethylsulfoxide (DMSO), polar lipids, or N-methyl-2-pyrrolidone, diethylene glycol monoethyl ether, calcipotriene, detergents, emollients, ethoxy diglycol, triacetin, benzyl alcohol, sodium laureth sulfate, dimethyl isosorbide, isopropyl myristate, medium chain triglyceride oil (MCT Oil), menthol, isopropyl isostearate, propylene glycol monostearate, lecithin, diisopropyl adipate, diethyl sebacate, oleic acid, ethyl oleate, glyceryl oleate, caprylic/capric triglyceride, propylene glycol dicaprylate/dicaprate, laureth 4, oleth-2, oleth-20, propylene carbonate, nonoxynol-9,2-n-nonyl-1,3-dioxolane, $C_7$ to $C_{14}$-hydrocarbyl substituted 1,3-dioxolane, 1,3-dioxine, or acetal and nonoxynol-15.

6. The process for the preparation of Rhein as claimed in claim 1, wherein the humectant is selected from glycerol, sorbitol, maltitol, polydextrose, triacetin, propylene glycol, polyethylene glycol (PEG) esters including PEG-20 stearate, PEG-40 stearate, PEG-150 stearate, PEG-150 distearate and PEG-100 stearate, alkoxylated alcohols including laureth-12, ceteareth-20, laureth-23, glycereth-7, glycereth-12, glycereth-26, PEG-4, PEG-6, PEG-8, PEG-12, PEG-32, PEG-75, PEG-150, dipropylene glycol, polypropylene glycol, pantothenol, gluconic acid salts.

7. The process for the preparation of Rhein as claimed in claim 1, wherein the thickening agent or gelling agent is selected from cellulose, hydroxypropyl cellulose ("HPC"), hydroxypropyl methyl cellulose, hydroxyethyl cellulose, methyl cellulose, acacia, alginic acid bentonite, polyvinyl pyrrolidone, magnesium aluminium silicate, carbomer, microcrystalline cellulose, carboxymethylcellulose calcium or sodium, cetostearyl alcohol, ethylcellulose, glycerin, gelatin, guar gum, hydroxypropyl cellulose, maltodextrin, polyvinyl alcohol, povidone, propylene carbonate, propylene glycol alginate, sodium alginate, sodium starch glycolate, starch, tragacanth, stearic acid and xanthan gum.

8. The process for the preparation of Rhein as claimed in claim 1, wherein the pH adjusting agent is selected from triethanolamine (TEA), citric acid monohydrate, amine base tromethamine, tetrahydroxypropyl ethylenediamine, diethanolamine, aminomethyl propanol, and/or sodium or ammonium hydroxide.

* * * * *